United States Patent [19]

Graf von Berckheim

[11] 4,056,772
[45] Nov. 1, 1977

[54] ION DETECTOR

[76] Inventor: Constantin Graf von Berckheim, Friedrichstrasse 9, Weinheim, Germany, 6940

[21] Appl. No.: 660,956

[22] Filed: Feb. 24, 1976

[30] Foreign Application Priority Data

Mar. 6, 1975 Germany .............................. 2509766

[51] Int. Cl.² ............................................ G01R 31/02
[52] U.S. Cl. .................................... 324/72; 324/133; 340/258 D
[58] Field of Search ..................... 324/72, 72.5, 51, 52, 324/133, 67; 340/253 Z, 255, 258 D

[56] References Cited

U.S. PATENT DOCUMENTS 3,482,235  12/1969  Johnson .................................. 324/72
3,878,459   4/1975  Hanna .................................... 324/133

Primary Examiner—M. Tokar
Attorney, Agent, or Firm—Burgess, Dinklage & Sprung

[57] ABSTRACT

An ion detector of simple construction and ease of operation comprising a space charge detector having a sensing electrode which detects the presence of a space charge by the charging of the sensing electrode, an evaluating circuit contained in a housing bearing the sensing electrode in the form of a surface electrode, and indicator means for indicating the presence or absence of ions depending on the charge on the sensing electrode.

11 Claims, 3 Drawing Figures

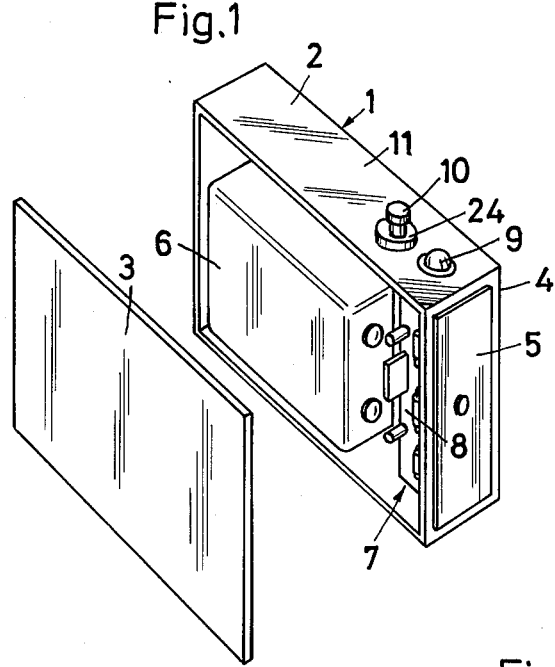
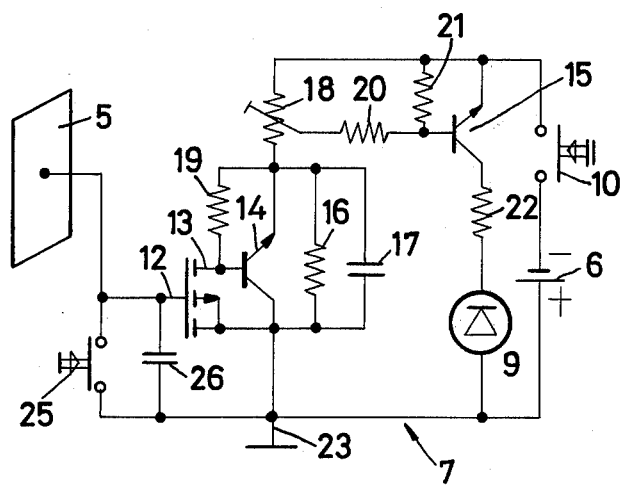
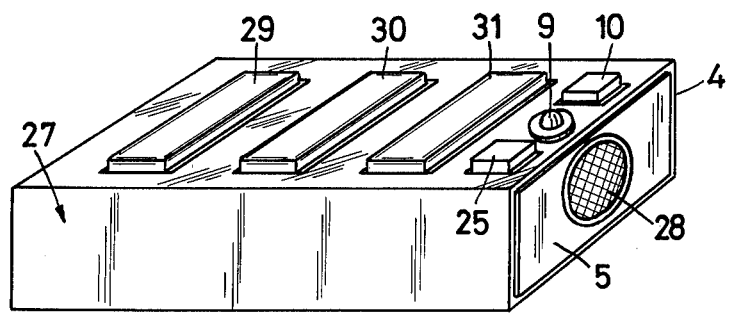

ized and indicated. In this manner the ion density
ION DETECTOR

BACKGROUND

The invention relates to an ion detector having a sensing electrode, an evaluating circuit, and an indicator means.

The known ion detectors are measuring instruments in which a blower drives the air being tested between two sensing electrodes to which a given voltage is applied. The deflection of the ions which takes place in the field between the sensing electrodes produces a reactive current whose magnitude is determined in the evaluating circuit and indicated. In this manner the ion density can be measured fairly accurately. The apparatus, however, is very expensive.

THE INVENTION

The invention is addressed to the task of devising a simply constructed and therefore inexpensive, easy-to-operate ion detector which will be capable of indicating a sufficient ionization.

This is accomplished with the invention, in that the ion detector is constructed as a space charge sensing device which detects the presence of a space charge through the charging of the sensing electrode, the evaluating circuit is contained in a housing of the size of a hand-held measuring apparatus, which is made substantially of insulating material and bears externally the sensing electrode, and the sensing electrode is in the form of a surface electrode extending along a wall of the housing.

Use is made of the fact that in many cases it is not necessary to measure the ion density. Instead it suffices to determine by means of a space charge sensor whether a sufficient number of ions is present. In this manner it is possible to know, for example, whether an ion generator is actually supplying ions or which parts of a space are insufficiently supplied with ions. If the ion density is too low, the sensing electrode will be charged not at all or very slowly by the space charge arising from the ions, and the indicator means will not respond or takes too long to do so. A high ion density will result in the immediate response of the indicator means and, if desired, can even be indicated in a roughly quantitative manner.

Only a few components are required for the space charge sensor. The housing can therefore be small and handy, and thus can be held easily in one hand. The apparatus can also be operated easily by the layman. Consequently, a person can take the ion detector in hand and test the place where he is to see whether a sufficient number of ions is present. The apparatus is also very inexpensive, so that anyone possessing an ion generator will be able to purchase an ion detector of this kind.

Since the surface electrode can be supported by the wall, thin and therefore inexpensive electrode materials will suffice. The surface electrode can even be deposited from a vapor. Since there is no need for any projecting parts, the danger of damage is slight and the apparatus thus becomes all the more easy to use. Furthermore, the surface electrode has a certain directional effect, which can be important in the case of ions being delivered by an air stream.

In a variant, the object of the invention is achieved in that the ion detector is in the form of a space charge sensing means which determines the pressure of a space charge through the charging of the sensing electrode, the evaluating circuit is contained in a housing of the size of a hand-held measuring apparatus which is made substantially of insulating material and bears the sensing electrode externally, and the housing is also the housing of a remote control device.

Since the components needed for the ion detector take very little space, there is no difficulty in using the housing of the remote control device also for the ion detector, while still retaining most of the previously mentioned advantages. Since such remote control devices are hand-held devices, the user has no need to change his general method of using them when they serve also as ion detectors. When a surface electrode that is mounted on a wall of the housing is used in this connection, the combined apparatus can have a directional action with regard to the remote controlling as well as a directional action with regard to the detection of ions.

In particular, the housing can be of an elongated brick shape and the surface electrode can be mounted on the smallest face thereof. The result is an especially manageable apparatus. If in addition an on-off pushbutton is provided on a surface adjacent the surface electrode, the ease of operation is further enhanced.

With special advantage, the indicator means is a light emitting diode which lights up when a predetermined state of charge develops on the sensing electrode. The light emitting diode as a rule has only two states, but it clearly indicates even to a layman whether or not ions are present in the desired minimum number.

The housing of an ultrasonic remote control of a television receiver is especially suitable for the housing also of an ion detector in accordance with the invention. A television viewer can then determine, by means of the remote control device which he is holding in his hand, whether the area around him is sufficiently supplied with ions.

It is even more desirable to use the housing of the ultrasonic remote control of an ion generator. A remote control of this kind makes it possible to turn on and off an ion generator and its corresponding blower, and to regulate them, if desired, when the supply of ions is insufficient, it being possible then to verify the effect of the ion generator.

Preferably, not only is the same housing used, but also the battery powering the remote control device supplies power to the evaluating circuit of the ion detector.

It is recommendable to connect the sensing electrode to the control terminal of an electronic driver circuit which controls the indicator means through an amplifier. In this manner even relatively weak states of charge will be clearly indicated.

In particular, the amplifier can have an adjusting means for adjusting the threshold of the response of the light emitting diode. This can be accomplished, for example, by a two-stage transistor amplifier in which the base of the second transistor is connected to the wiper contact of a potentiometer in the output circuit of the first transistor. In this manner it is possible to set precisely the state of charge on the sensing electrode to which the light emitting diode is to respond.

It is especially advantageous for the driver circuit to use a field effect transistor. This transistor can have a very high input resistance so that the charge on the sensing electrode will not be carried away faster than it can be built up, and this results in an appreciable amplifying effect.

The invention will now be further explained with reference to the drawing, wherein FIG. 1 is a perspective view of a first embodiment, FIG. 2 is a diagrammatic representation of a circuit embodiment, and FIG. 3 is a perspective view of a second embodiment.

FIG. 1 represents a brick-shaped plastic housing 1 consisting of a box 2 with cover 3. On the smallest, end face 4 of housing 1 there is a surface electrode 5. Within the housing 1 there is contained a battery 6 and an evaluating circuit 7 having a variety of components mounted on a board 8. An indicator means in the form of a light emitting diode 9 and a pushbutton 10 extend outwardly through a side wall 11 of the housing 1 adjoining the end wall 4.

The composition of the evaluating circuit 7 can be seen in FIG. 2. The surface electrode 5 is connected to the control terminal 12 of a driver circuit 13 in the form of a field effect transistor. The field effect transistor can be, for example, a metal oxide silicon transistor. Its output drives a two-stage amplifier having a first transistor 14 and a second transistor 15. The collector and emitter of transistor 14 are connected together by a resistor 16 and a condenser 17, and the collector is connected in series with a potentiometer 18. Another resistance 19 is connected between the base and the collector of this transistor 14. The wiper contact of the potentiometer 18 is connected through a resistor 20 to the base of transistor 15. The base and the collector of this transistor are connected together by a resistor 21. The emitter of transistor 15 is connected through a resistor 22 to the light emitting diode 9. When the battery 6 is connected to the circuit by pushbutton switch 10 and a sufficient charge has collected on the surface electrode 5, the gate 13 carries such a current that the transistor 14 conducts. As soon as this current has reached such a value that the potential at the wiper contact of potentiometer 18 is sufficient to cause transistor 15 to conduct, the diode 9 begins to emit light. This circuit is so designed that it responds to negative ions.

Additionally, a ground connection 23 can be provided, which can be connected, for example, to the externally located metal lock ring 24 of the pushbutton 10. Thus it will be possible by simultaneously touching this metal ring 24 and the surface electrode 5 to produce a rapid discharge of this electrode.

Instead of this, an additional discharge pushbutton 25 can be located between the positive pole of battery 6 and the surface electrode 5. This discharge button can be mechanically coupled contrariwise with the pushbutton 10. By means of a condenser 26, the potential of the surface electrode 5 can be better matched to that of the rest of the circuit.

In the embodiment shown in FIG. 3, the housing 27 of an ultrasonic remote control of an ion generator is used also as the housing for the ion detector. Parts 5, 9, 10 and 25 correspond to those in FIGS. 1 and 2. In the center of the electrode 5 there is provided a transmission aperture 28 for an ultrasonic transmitter, which is adapted for the transmission of different ultrasonic signals when the keys 29, 30 and 31 are depressed. For example, key 29 turns on an ion generator, key 30 sets at low speed a fan blowing air through the ion generator, and key 31 sets the fan at high speed. In each case a second depression of the keys turns off the corresponding device.

An ultrasonic remote control system of this kind can also be used in a known manner for the remote controlling of a television receiver. The various keys then each serve different functions. Since the construction of such apparatus is known there is no need to describe them further.

In any case, numerous simplifications can be undertaken within the housing 27, by using certain parts, such as the battery, in common for the remote control circuit and for the evaluating circuit.

It will be understood that the specification and examples are illustrative but not limitative of the present invention and that other embodiments within the spirit and scope of the invention will suggest themselves to those skilled in the art.

What is claimed is:

1. Remote control ion detector and controller for a remotely spaced controllable ion generator comprising a space charge detector having a sensing electrode which detects the presence of a space charge by the charging of the sensing electrode, an evaluating circuit contained in a housing consisting essentially of insulating material and bearing the said sensing electrode externally, wherein the sensing electrode is in the form of a surface electrode extending along a wall of said housing, indicator means for indicating the presence or absence of ions and an ultrasonic remote control device for controlling the ion generator as a result of the indication by the indicator means.

2. Ion detector and controller as claimed in claim 1 wherein the housing is in the shape of an elongated brick and the surface electrode is disposed on the smallest brick face.

3. Ion detector and controller as claimed in claim 2 wherein a pushbutton switch to discharge the said electrode by connection same to a ground is provided.

4. Ion detector and controller of claim 1 wherein the indicator means is a light emitting diode which lights up upon the attainment of a specific state of charge on the sensing electrode.

5. Ion detector and controller as claimed in claim 1 wherein the housing houses an ultrasonic remote control device for a television receiver adjacent the ion generator 6. Ion detector and controller as claimed in claim 1 wherein a battery for the remote control device also supplies the evaluating circuit.

7. Ion detector and controller as claimed in claim 1 wherein the sensing electrode is connected to the control terminal of an electronic driver circuit which drives the indicator through an amplifier.

8. Ion detector and controller as claimed in claim 7 wherein the amplifier has an adjusting means for the adjustment of the response value of the light emitting diode.

9. Ion detector and controller as claimed in claim 8 wherein the amplifier is a two-stage transistor amplifier in which the base of the second transistor is connected to the wiper contact of a potentiometer in the output circuit of the first transistor.

10. Ion detector and controller as claimed in claim 7 wherein the driver circuit comprises a field effect transistor.

11. Ion detector and controller, for a spaced controllable ion generator, disposed in a remote control device having the shape of an elongated brick which ion detector comprises a space charge detector having a sensing electrode which detects the presence of a space charge by the charging of the sensing electrode, an evaluating circuit contained in a housing consisting essentially of insulating material and bearing the said sensing electrode externally, wherein the sensing electrode is in the form of a surface electrode disposed along the smallest brick face of said brick-shaped remote control device, indicator means for indicating the presence or absence of ions and an ultrasonic remote control device for controlling the ion generator as a result of the indication by the indicator means.

* * * * *